United States Patent
Chiolini et al.

(10) Patent No.: US 9,596,881 B2
(45) Date of Patent: Mar. 21, 2017

(54) COMPOSITION FOR ELECTRONIC CIGARETTES

(71) Applicant: DKS AROMATIC S.R.L., Corsico (MI) (IT)

(72) Inventors: Alessandro Chiolini, Corsico (IT); Roberto Chiolini, Corsico (IT)

(73) Assignee: DKS AROMATIC S.R.L., Corsico (MI) (IT)

( * ) Notice: Subject to any disclaimer, the term of this patent is extended or adjusted under 35 U.S.C. 154(b) by 0 days.

(21) Appl. No.: 14/365,813

(22) PCT Filed: Dec. 14, 2012

(86) PCT No.: PCT/IB2012/002706
§ 371 (c)(1),
(2) Date: Jun. 16, 2014

(87) PCT Pub. No.: WO2013/088230
PCT Pub. Date: Jun. 20, 2013

(65) Prior Publication Data
US 2014/0366902 A1    Dec. 18, 2014

(30) Foreign Application Priority Data

Dec. 16, 2011  (IT) ................ MI2011A2290

(51) Int. Cl.
*A24B 15/10* (2006.01)
*A61K 47/10* (2006.01)
*A24B 15/16* (2006.01)
*A61K 9/00* (2006.01)

(52) U.S. Cl.
CPC .............. *A24B 15/10* (2013.01); *A24B 15/16* (2013.01); *A61K 9/007* (2013.01); *A61K 47/10* (2013.01)

(58) Field of Classification Search
USPC ........ 435/132, 155, 157, 159, 158; 131/337, 131/352
See application file for complete search history.

(56) References Cited

U.S. PATENT DOCUMENTS

| | | | |
|---|---|---|---|
| 7,928,148 B2 * | 4/2011 | Bloom | C07C 29/60 514/738 |
| 9,004,073 B2 * | 4/2015 | Tucker | H01C 17/00 128/202.21 |
| 2002/0016469 A1 * | 2/2002 | Hughes | C07D 401/04 546/279.4 |
| 2004/0002520 A1 | 1/2004 | Soderlund et al. | |
| 2008/0103340 A1 | 5/2008 | Binder et al. | |
| 2010/0196964 A1 * | 8/2010 | Boy | A23J 1/125 435/89 |
| 2010/0236562 A1 * | 9/2010 | Hearn | A61K 31/465 131/330 |
| 2011/0005535 A1 | 1/2011 | Xiu | |
| 2011/0036365 A1 | 2/2011 | Chong et al. | |

FOREIGN PATENT DOCUMENTS

| | | |
|---|---|---|
| EP | 1 618 803 | 1/2006 |
| KR | 2010 0028182 | 3/2010 |
| WO | WO 01/16063 | 3/2001 |
| WO | WO 2010/008951 | 1/2010 |

OTHER PUBLICATIONS

International Search Report for PCT/IB2012/002706 mailed Mar. 22, 2013.
Written Opinion of the International Searching Authority mailed Mar. 22, 2013.
Italian Search Report for IT MI2011A002290 dated Jun. 21, 2012.
M. Dasari et al., "Low-Presssure Hydrogenolysis of Glycerol to Propylene Glycol", Applied Catalysis A; General, Elsevier Science, vo. 281, No. 1-2, Mar. 8, 2005, pp. 225-231.
E. Tronconi et al., "A Mathematical Model for the Catalytic Hydrogenolysis of Carbohydrates", Chemical Engineering Science, vol. 47, No. 9-11, Jun. 1, 1992, pp. 2451-2456.
A. McQueen et al., "Interviews with Vapers: Implications for Future Research with Electronic Cigarettes", Nicotine & Tobacco Research, Carfax, Sep. 1, 2011, vol. 13, No. 9, pp. 860-867.
Vapouriz, Why Use Vapouriz Electronic Cigarettes ? Vegetable Glycerine 101 >>, online filing, Nov. 16, 2011, 1 page.
S. Pedersen, "Chemicals from Sugars" Topsoe Catalysus Forum, online filing, Aug. 22, 2008, 17 pages.
Novepha Company Limited, 'Bio=Propylene Gylcol (Bio-PG), online filing, 2010, XP002677445, 1 page.

\* cited by examiner

*Primary Examiner* — Dennis Cordray

(57) ABSTRACT

The present invention relates to a new vegetable-based composition for liquid to be vaporized in electronic cigarettes, comprising water and propylene glycol of vegetable origin and/or glycerol and/or nicotine and/or natural flavors.

5 Claims, No Drawings

COMPOSITION FOR ELECTRONIC CIGARETTES

This application is the U.S. national phase of International Application No. PCT/IB2012/002706 filed 14 Dec. 2012 which designated the U.S. and claims priority to IT MI2011 A002290 filed 16 Dec. 2011, the entire contents of each of which are hereby incorporated by reference.

FIELD OF THE INVENTION

The present invention relates to a new vegetable-based composition for liquid to be vaporized in electronic cigarettes.

PRIOR ART

The electronic cigarette (e-cigarette) is a device that emulates the traditional products for smoking tobacco, particularly traditional cigarettes. The device uses heat to vaporize a liquid solution containing water, propylene glycol and/or glycerol and/or nicotine and/or natural flavors to reproduce the physical sensation and aroma of the smoke of traditional cigarettes.

As known, cigarette smoking creates very strong dependence in subjects and, because of the multiple toxic substances which develop during the combustion of tobacco and additives present therein, is one of the main causes of the formation of tumors and diseases of the respiratory and circulatory apparatuses. Electronic cigarettes are used as an alternative to smoking traditional tobacco or even as a tool to quit smoking, because they allow users to maintain the taste of smoking without incurring in health risks normally associated with tobacco.

A wide range of compositions are also available for vaporizable liquids containing different flavors, such as vanilla, mint or cherry, not containing nicotine and that therefore do not create addiction. The electronic cigarettes can therefore be used by non smoking consumers also for recreational purposes.

The electronic cigarettes have three essential components: a filter generally made of plastic material, which acts as a mouthpiece, wherein a cartridge containing the solution to be vaporized is housed. The cartridge, once exhausted, can be manually charged with another liquid, which can be purchased pre-mixed or by purchasing individual components and mixing them in variable compositions according to individual taste. The second component is the atomizer. This device heats the liquid contained in the cartridge and, without combustion, allows to create a gaseous suspension containing substances present in the liquid. The effect of smoking is primarily conferred by glycerol and, minimally, by propylen glycol. The third component is the battery, usually a rechargeable lithium battery. There are two types of batteries: the first comprises a sensor inside that detects the pressure difference that occurs during aspiration and activates the battery, allowing the operation of the vaporizer. The second type, manual, is provided with an external button which, once pressed, allows the activation of the battery, and therefore the operation of the vaporizer. The duration of the pressure on the button also determines the density of the smoke produced, in order to produce different user satisfaction.

The liquid solutions contained in the cartridges can have variable compositions, but are generally based on water and hygroscopic components, such as propylene glycol and/or glycerol and/or polyethylene glycol, which trap the water vapor formed during the heating of the water and allow the release through the mouthpiece. The remaining portion of the liquid contained in the cartridge contains nicotine and/or flavors.

The propylene glycol usually used is of mineral origin and is obtained by chemical synthesis from propylene, a gas produced from fossil fuels, passing through the intermediate propylene oxide which is then hydrated to give the propylene glycol.

Glycerol is mainly produced by saponification of fats as a byproduct of the production of soap.

A flavor is defined as sensory characteristic given by a food or other substance resulting from the combination of taste and odor. The flavors are used in the food, cosmetic and tobacco industry. In particular, there are three categories: natural flavors extracted from natural products, natural flavors identical to natural products but obtained by chemical synthesis and synthetic flavors not present in nature and obtained by chemical synthesis. In the case of electronic cigarettes a number of different flavors of different origins can be added to the composition, from those that attempt to reproduce the flavor of traditional cigarettes to those instead of food type, such as vanilla and coffee. The use of electronic cigarettes is therefore expected also for recreational purposes, using compositions based on flavors such as vanilla, mint or cherry.

Nicotine is a psychoactive alkaloid found naturally in the tobacco plant that gives high dependence in smokers. In electronic cigarettes, nicotine may be present or not in the formulations and its concentration can vary depending on the preferences of the consumer. For example, liquids with a low content of nicotine have a nicotine concentration of about 6-8 mg/ml of liquid, instead liquids with a very high dose of nicotine have a nicotine concentration of about 24-36 mg/ml. Electronic cigarettes containing nicotine may therefore be used as an alternative to traditional cigarettes, even for smoking in public places where normally it is not allowed, or as a tool to quit smoking.

In recent years, there has been an increased awareness of the world population concerning environment preservation, use of energy resources and health. Therefore, there is a growing trend towards the use of more "natural" products as possible, understood as being less harmful to the ecosystem and one's own body. Is known that the intensive exploitation of fossil carbon, that produces coal, natural gas and gasoline, is slowly leading to a depletion of available energy resources. To date many other products extracted or derived from fossil carbon have been employed, not used as an energy source, such as propylene glycol. The mineral origin of this compound, for instance, used as a solvent for pharmaceutical preparations, as a food additive or as a vehicle for fragrances, does not guarantee purity and it is possible that in its formulations traces of solvents or toxic substances are present. In addition, its wide use contributes to the depletion of non-renewable energy sources.

Another problem that the world population became aware of, is the increasing loss of the authenticity of natural flavors and fragrances, which are increasingly being replaced or enhanced by the use of synthetic flavors that create or amplify sensory characteristics not found in nature.

OBJECTS OF THE INVENTION

An object of the present invention is therefore to provide a liquid to be vaporized in electronic cigarettes based on a composition entirely of vegetable origin.

A further object of the present invention is to provide a composition for liquid to be vaporized in electronic cigarettes, which comprises flavors of entirely natural origin.

Still a further object of the present invention is to provide a composition for liquid to be vaporized in electronic cigarettes, which does not consume non-renewable energy resources.

DESCRIPTION OF THE INVENTION

These and still other objects which will be better clarified hereinafter are achieved by the present invention which relates to a composition for liquids intended for electronic cigarettes comprising water and propylene glycol of vegetable origin and/or glycerol and/or nicotine and/or natural flavors.

Preferably, the present invention relates to a composition for liquids intended for electronic cigarettes, which comprises water, propylene glycol, glycerol and natural flavors.

Preferably, the present invention relates to a composition for liquids intended for electronic cigarettes, which comprises water, propylene glycol, glycerol and nicotine.

Preferably, the present invention relates to a composition for liquids intended for electronic cigarettes, which comprises water, propylene glycol, glycerol, nicotine and natural flavors.

According to the present invention, the propylene glycol employed in the present composition is a product of vegetable origin, derived from maize. According to a process for its preparation, the maize is first wet milled in order to obtain as basic products, for example, starch, gluten, fibers and maize oil. The starch is then saccharified via enzymatic means, according to known techniques, to produce glucose, which is further converted to sorbitol by catalytic hydrogenation. The sorbitol, in turn, is subjected to further catalytic hydrogenation at high temperature and pressure to obtain its fragmentation to propylene glycol, ethylene glycol and butanediol.

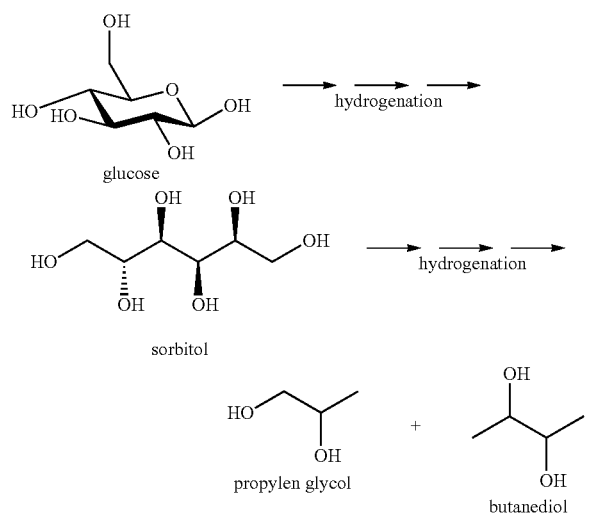

The mixture of glycols thus obtained is then separated into individual products.

Thus it appears evident that the origin of propylene glycol thus obtained is entirely vegetable and not mineral, given that there is no use of fossil carbon.

Glycerol is mainly produced by saponification of fats as a byproduct of soap production. In particular, the glycerol according to the invention is of food grade vegetable origin, derived from palm oil and/or coconut.

The nicotine, that may be present in the composition according to the invention, can be of natural origin, obtained by extraction from tobacco leaves, or obtained by chemical synthesis.

According to the present invention, the flavors that may be present in the composition for liquids intended for electronic cigarettes are of natural origin i.e. only extracted from products present in nature. The natural flavors are made from natural raw materials by chemical-physical, enzymatic or microbiological processes and contain no artificial or natural identical aromatic substance, as defined above.

The composition according to the invention may also contain food grade alcohols and any further additives and excipients.

An advantage of the present invention is therefore to offer a chance to the user of electronic cigarettes to consume a product of wholly natural base and of vegetable origin. The invention is directed to a wide range of users, given the wide variety of flavors available and given the growing interest in products of natural origin, that would respect the environment, not harmful to the consumer and would maintain unchanged as much as possible the tastes and the flavors of the products found in nature. In particular, the present invention is directed to users already sensitized and with a greater environmental awareness, whose life style is devoted to research of mental-physical and environmental well-being and to reduce consumption of natural resources and energy. In addition, the concept of smoking electronic cigarettes ("vapers") is a growing trend, which has no contraindication to the health and provides a sensory gratification, without creating dependency. The appearance of the recreational "vapers" also consists in selecting, from time to time, the use of the most different flavors. A further advantage of the present invention consists in being able to use electronic cigarettes in public places, where it would normally be prohibited.

This is given by the fact that is emitted simple flavored water vapor, not resulting from the combustion that generates, as in traditional cigarettes, toxic substances.

As always in accordance to the present invention the composition for liquids intended for electronic cigarettes comprises the different components in the following percentage intervals, expressed as weight percentage based on the total weight of the composition (w/w).

The propylene glycol and/or glycerol are then comprised in a range between 70% and 95% by weight, preferably between 80% and 90% and in particular they are present at 90%.

Regarding the flavors, these are comprised in a range between 5% and 0.01% by weight, preferably between 2% and 0.5%, most preferably between 1% and 0.5% and in particular they are present at 1%.

The water and any food grade alcohols and any further additives and excipients, are comprised in a range between 10% and 1% by weight approximately and in any case to bring to 100% the weight of the composition.

A preferred composition according to the present invention comprises:
propylene glycol and glycerol at 90% by weight
ethyl alcohol at 6% by weight
water at 6% by weight
flavors at 1% by weight The vegetable origin of propylene glycol used according to the present invention is easily analytically detectable using the technique of gas-chromatography combined with mass spectrometry (GC-MS). By way of the above analysis, the peak related to the propylene glycol is instantly identifiable and accompanied by detectable traces of 2,3-butanediol, a byproduct of the passage from sorbitol to propylene glycol. With the analysis by gas chromatography - mass spectrometry of propylene glycol according to prior art, the peak relative to propylene glycol is always detectable, but the peak relative to the 2,3-butanediol is not present, being the synthesis method completely different and having as starting products in one case the carbon fossils (according to prior art) and in the other the maize (according to the invention).

A sample of propylene glycol of mineral origin and a sample of propylene glycol of vegetable origin was examined, in order to investigate the presence of 2,3-butanediol as a marker of the vegetable origin of the propylene glycol.

The preparation of the sample involves the dilution to 15% (w/w) with highly purified water (Ph. Eur.).

The analysis was carried out using the gas-chromatography technique combined with mass spectrometry (GC-MS). The GC part was carried out using the split technique, injecting 0.5 μl of sample, suitably diluted. The mass detector used is of the type with single quadrupole and which uses the electronic impact as ionization technique. The recognition of peaks was made by comparison with the reference spectra of a library NIST 98.

The survey has revealed the presence of 2,3-butanediol only in the sample of propylene glycol of vegetable origin; this then allows to identify the 2,3-butanediol as a marker of particular vegetable origin of propylene glycol, according to the present invention, where "propylene glycol of vegetable origin" means that obtained from maize, through passages into starch, glucose and sorbitol described above.

Materials and Methods for the GC-MS Analysis

Sample A: propylene glycol of vegetable origin (according to the invention)
Sample B: propylene glycol of mineral origin (according to prior art)
Thinner: highly purified water Ph. Eur.
Preparation of samples:
both samples of propylene glycol were diluted to 15% (w/w) with water.
Gas-Chromatographer
Model: Trace GC 2000
Brand: ThermoFinnigan
Oven Setting
Initial temperature (° C.): 70
Stop (min): 5
Number of ramps: 2
Ramp 1 (° C./min): 5
Final Temperature 1 (° C.): 190
Stop (min): 11
Ramp 2 (° C./min): 15
Final Temperature 2 (° C.): 300
Stop (min): 10
Injector setting
Temperature (° C.): 250
Mode: split
Split flow (ml/min): 110
Carrier
Gas carrier: Helium
Mode: constant flow
Flow (ml/min): 1.10
Injection volume (μl): 0.5
Mass detector
model: Trace MS
brand: ThermoFinnigan
type: single quadrupole
ionization modes: electronic impact
ionization energy (eV): 70
Detector voltage (V): 400.0
Source temperature (° C.): 200
Interface temperature GC (° C.): 250
Acquisition mode: full scan
Gas-chromatography column:
brand: Zebron
model: ZB-5 ms
length (m): 30
internal diameter (mm): 0.25
thickness of the inner lining (gm): 0.25.

For illustration only and not limitative purposes of the present invention are given below some examples of embodiments.

Example 1

The composition for liquids intended for electronic cigarettes comprises:
food grade propylen glycol of vegetable origin (maize) at 65% by weight
food grade glycerol of vegetable origin (palm or coconut) at 25% by weight
food grade ethyl alcohol at 6% by weight
water at 3% by weight
cinnamon natural flavor at 1% by weight.
Said cinnamon natural flavor is essential oil of cinnamon bark obtained by extraction in a steam current.

Example 2

The composition for liquids of electronic cigarettes comprises:
food grade propylene glycol of vegetable origin (maize) at 65% by weight
food grade glycerol of vegetable origin (palm or coconut) at 25% by weight
food grade ethyl alcohol at 6% by weight
water at 3% by weight
bergamot natural flavor at 1% by weight.
Said natural bergamot flavor is obtained by cold pressing bergamot peel.

The invention claimed is:

1. A process for the manufacture of liquid composition for electronic cigarettes comprising at least water, propylene glycol of vegetable origin and glycerol, said process comprising:
forming said propylene glycol by milling maize to provide starch and other products, reacting said starch via enzymatic saccharification to provide glucose, converting said glucose to sorbitol by catalytic hydrogenation, converting said sorbitol to said propylene glycol by catalytic hydrogenation, and extracting and purifying said propylene glycol,
deriving said glycerol from palm oil and/or coconut oil to form glycerol of food grade vegetable origin,
providing water, and
combining at least said water, said propylene glycol of vegetable origin and said glycerol.

2. The process according to claim 1, wherein the liquid composition further comprises nicotine and natural flavors.

3. The process according to claim 1, wherein said propylene glycol is characterized by a spectra exhibiting a peak that indicates 2,3-butanediol.

4. The process according to claim 2, further comprising providing the liquid composition to an electronic cigarette cartridge to be vaporized.

5. A process for the manufacture of a composition for liquids for electronic cigarettes comprising water, propylene glycol of vegetable origin, glycerol, nicotine and natural flavors, said process comprising:
  forming said propylene glycol by milling maize to provide starch and other products, reacting said starch via enzymatic saccharification to provide glucose, converting said glucose to sorbitol by catalytic hydrogenation, converting said sorbitol to said propylene glycol by catalytic hydrogenation, and extracting and purifying said propylene glycol,
  deriving said glycerol from palm oil and/or coconut oil to form glycerol of food grade vegetable origin,
  providing water, food grade ethyl alcohol and bergamot natural flavor; and
  combining said water, said propylene glycol of vegetable origin, said glycerol, said food grade ethyl alcohol, said bergamot natural flavor and nicotine.

* * * * *